(12) United States Patent
Miyamoto et al.

(10) Patent No.: US 10,376,460 B2
(45) Date of Patent: Aug. 13, 2019

(54) FLAVORING AGENT AND COMPOSITION FOR ORAL CAVITY CONTAINING SAME

(71) Applicant: NOF CORPORATION, Tokyo (JP)

(72) Inventors: Koji Miyamoto, Kawasaki (JP); Nobuyuki Yamamoto, Kawasaki (JP); Shunsuke Sakurai, Kawasaki (JP); Yoshihisa Shimamura, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 15/738,991

(22) PCT Filed: Jun. 30, 2016

(86) PCT No.: PCT/JP2016/069369
§ 371 (c)(1),
(2) Date: Dec. 21, 2017

(87) PCT Pub. No.: WO2017/002981
PCT Pub. Date: Jan. 5, 2017

(65) Prior Publication Data
US 2018/0168987 A1 Jun. 21, 2018

(30) Foreign Application Priority Data
Jun. 30, 2015 (JP) .................................. 2015-131083

(51) Int. Cl.
| | | |
|---|---|---|
| *A61K 8/81* | (2006.01) | |
| *A61Q 11/00* | (2006.01) | |
| *C08F 220/36* | (2006.01) | |
| *C08F 230/02* | (2006.01) | |
| *A61K 8/24* | (2006.01) | |
| *A61K 8/34* | (2006.01) | |
| *A61K 8/362* | (2006.01) | |
| *A61K 8/41* | (2006.01) | |
| *A61K 8/43* | (2006.01) | |
| *A61K 8/60* | (2006.01) | |
| *A61K 8/67* | (2006.01) | |
| *A61K 47/32* | (2006.01) | |

(52) U.S. Cl.
CPC .............. *A61K 8/8152* (2013.01); *A61K 8/24* (2013.01); *A61K 8/347* (2013.01); *A61K 8/362* (2013.01); *A61K 8/416* (2013.01); *A61K 8/43* (2013.01); *A61K 8/604* (2013.01); *A61K 8/676* (2013.01); *A61K 8/8158* (2013.01); *A61Q 11/00* (2013.01); *C08F 220/36* (2013.01); *C08F 230/02* (2013.01); *A61K 47/32* (2013.01); *A61K 2800/74* (2013.01)

(58) Field of Classification Search
None
See application file for complete search history.

(56) References Cited

U.S. PATENT DOCUMENTS 4,992,259 A * 2/1991 Schiraldi ................ A61Q 11/00
424/49
2017/0281502 A1 10/2017 Miyamoto et al.

FOREIGN PATENT DOCUMENTS

| JP | H11-035605 A | 2/1999 | |
|---|---|---|---|
| JP | 2000-178152 A | 6/2000 | |
| JP | 2002-212041 A | 7/2002 | |
| JP | 2004-189678 A | 7/2004 | |
| JP | 2004-196868 A | 7/2004 | |
| JP | 2006-27367 | * 10/2006 | ............ A61Q 11/00 |
| JP | 2006-273767 A | 10/2006 | |
| JP | 2008-007414 A | 1/2008 | |
| JP | 2011-153101 A | 8/2011 | |
| JP | 2013-018749 A | 1/2013 | |
| JP | 2014-040408 A | 3/2014 | |
| JP | 2016-037455 A | 3/2016 | |
| WO | WO 2016/031461 A1 | 3/2016 | |

OTHER PUBLICATIONS

Yarmolinsky et al., "Common Sense about Taste: From Mammals to Insects," *Cell*, 139(2): 234-244 (2009).
Japanese Patent Office, International Search Report in International Patent Application No. PCT/JP2016/069369 (dated Sep. 6, 2016).

* cited by examiner

*Primary Examiner* — Brian Gulledge
(74) *Attorney, Agent, or Firm* — Leydig, Voit & Mayer, Ltd.

(57) ABSTRACT

Provided by the present invention is a corrigent composed of a copolymer having a weight average molecular weight of 10,000-5,000,000 and comprising 10-90 mol % of a constitution unit based on 2-(meth)acryloyloxyethylphosphoryl choline, and
90-10 mol % of a (meth)acrylic monomer containing an alkyl group, a (meth)acrylic monomer containing a quaternary ammonium group and a constitution unit based on a (meth)acrylamide monomer. The present invention also provides a composition for mouth cavity containing the corrigent.

12 Claims, No Drawings

US 10,376,460 B2

FLAVORING AGENT AND COMPOSITION FOR ORAL CAVITY CONTAINING SAME

CROSS-REFERENCE TO RELATED APPLICATIONS

This patent application is the U.S. national phase of International Patent Application No. PCT/JP2016/069369, filed on Jun. 30, 2016, which claims the benefit of Japanese Patent Application No. 2015-131083, filed Jun. 30, 2015, the disclosures of which are incorporated herein by reference in their entireties for all purposes.

TECHNICAL FIELD

The present invention relates to a corrigent comprising a (meth)acrylic copolymer containing a phosphoryl choline group and a composition for mouth cavity that contains the corrigent.

BACKGROUND ART

Generally, in compositions for mouth cavity, various active ingredients such as a surfactant for imparting washing and foaming actions to the preparation, an antimicrobial agent as an active ingredient and an antiseptic for preventing microbial contamination during use are often blended as formulation design. Some of such active ingredients have uncomfortable tastes such as a strong bitter taste, rough taste or harsh taste. However, to ensure effectiveness, it is not preferable to reduce the amount thereof. To reduce uncomfortable tastes, therefore, a sweetening agent, algefacient, flavor and the like are blended expecting a taste masking effect (e.g., patent documents 1, 2).

Techniques using a cationic polymer (patent document 3) or a betaine type polymer (patent document 4) are known to mitigate the stimulating tastes and mitigate the hypersensitive components. To decrease the uncomfortable tastes, addition of a corrigent in addition to these polymers is still necessary.

However, a mere addition of a corrigent in addition to various active ingredients sometimes fails to solve the problem of uncomfortable tastes. There are individual differences in the strength of perception of each of five basic tastes (bitterness, sweetness, saltiness, umami, sourness). By adding a corrigent to reduce a certain kind of uncomfortable taste, an adverse effect phenomenon often occurs to increase a different kind of uncomfortable taste depending on the person. Since the molecular mechanism causing interactions of tastes is hardly elucidated (non-patent document 1), and it is necessary to repeat trial and error of seasoning every time the kind of the active ingredient changes slightly, so as to eliminate uncomfortable tastes for various people. On the other hand, (meth)acrylic copolymers containing a phosphoryl choline group have been utilized for cosmetics and skin external preparations (e.g., patent document 5); however, mitigation of stimulating tastes and mitigation of hypersensitive components such as the above-mentioned betaine-type polymers have not been studied.

As mentioned above, a corrigent that reduces any uncomfortable tastes relating to the five basic tastes without limitation to a particular taste property has been desired to eliminate uncomfortable tastes of a composition for mouth cavity.

DOCUMENT LIST

Patent Documents patent document 1: JP-A-2000-178152
patent document 2: JP-A-2002-212041
patent document 3: JP-A-2014-040408
patent document 4: JP-A-2006-273767
patent document 5: JP-A-2008-007414

Non-Patent Document non-patent document 1: Yarmolinsky et al., Cell, vol. 139, pages 234-244, 2009

SUMMARY OF THE INVENTION

Problems to be Solved by the Invention

Thus, the problem of the present invention is to provide a corrigent that reduces uncomfortable tastes while maintaining the balance of tastes of the preparation, and a composition for mouth cavity that contains the corrigent and has good taste masking property.

Means of Solving the Problems

The present inventors have conducted intensive studies in an attempt to solve the aforementioned problems and found that any uncomfortable tastes relating to the five basic tastes (bitterness, sweetness, saltiness, umami, sourness) are reduced when a particular 2-(meth)acryloyloxyethylphosphoryl choline (hereinafter abbreviated as MPC) copolymer is used as a corrigent, which resulted in the completion of the present invention.

That is, the present invention provides the following [1]-[23].

[1] A corrigent consisting of a copolymer having a weight average molecular weight of 10,000-5,000,000 and comprising 10-90 mol % of a constitution unit. (A1) based on 2-(meth)acryloyloxyethylphosphoryl choline, and 90-10 mol % of at least one kind of constitution unit selected from the group consisting of a constitution unit (B1) based on a (meth)acrylic monomer containing alkyl group, a constitution unit (B2) based on a (meth)acrylic monomer containing a quaternary ammonium group, and a constitution unit (B3) based on a (meth)acrylamide monomer.

[2] The corrigent of [1] wherein the copolymer has a weight average molecular weight of 10,000-5,000,000 and comprises 10-90 mol % of the constitution unit (A1) based on 2-(meth)acryloyloxyethylphosphoryl choline, and 90-10 mol % of at least one kind of constitution unit selected from the group consisting of the constitution unit (B2) based on (meth)acrylic monomer containing a quaternary ammonium group and the constitution unit (B3) based on (meth)acrylamide monomer.

[3] The corrigent of [1] or [2] which is a corrigent for reducing an uncomfortable taste relating to one or two or more senses of taste selected from the group consisting of bitterness, sweetness, saltiness, umami and sourness.

[4] The corrigent of [3] which is a corrigent for reducing an uncomfortable taste relating to one or two or more senses of taste selected from the group consisting of sweetness, saltiness, umami and sourness.

[5] The corrigent of [3] which is a corrigent for reducing an uncomfortable taste relating to bitterness, sweetness, saltiness, umami and sourness.

[6] A composition for mouth cavity, which comprises 0.001-5 mass % of the corrigent of any of the aforementioned [1] to [5], and 30.0-99.9 mass % of water.

[7] The composition for mouth cavity of [6], which further comprises one or two or more components selected from the group consisting of
1) at least one bitterness component selected from the group consisting of methyl salicylate, epsilon-aminocaproic acid, tranexamic acid, dequalinium chloride, benzalkonium chloride, benzethonium chloride, chlorhexidine hydrochloride, chlorhexidine gluconate, povidoneiodine, polyoxyethylenelauryl ether (8-10 E.O.), sodium lauroylsarcosinate, polyoxyethylene hydrogenated castor oil, sorbitan fatty acid ethylene adduct and tee extract;
2) at least one sweetness component selected from the group consisting of glycyrrhizin acid and a salt thereof;
3) at least one saltiness component selected from the group consisting of potassium nitrate, sodium ascorbate, disodium dihydrogen pyrophosphate, sodium pyrophosphate, and sodium chloride; and
4) at least one sourness component selected from the group consisting of aluminum lactate, ascorbic acid, pyridoxine hydrochloride, malic acid, citric acid, tartaric acid, vitamin C, disodium edetate, trisodium edetate, tetrasodium edetate, sodium citrate, gluconic acid, phosphoric acid, succinic acid and edetic acid.

[8] A method of reducing an uncomfortable taste, which comprises adding a copolymer having a weight average molecular weight of 10,000-5,000,000 and comprising
10-90 mol % of a constitution unit (A1) based on 2-(meth)acryloyloxyethylphosphoryl choline, and
90-10 mol % of at least one kind of constitution unit selected from the group consisting of a constitution unit (B1) based on a (meth)acrylic monomer containing an alkyl group, a constitution unit (B2) based on a (meth)acrylic monomer containing a quaternary ammonium group and a constitution unit (B3) based on a (meth)acrylamide monomer.

[9] The method of [8] wherein the copolymer has a weight average molecular weight of 10,000-5,000,000 and comprises 10-90 mol % of the constitution unit (A1) based on 2-(meth)acryloyloxyethylphosphoryl choline, and
90-10 mol % of at least one kind of constitution unit selected from the group consisting of the constitution unit (B2) based on a (meth)acrylic monomer containing a quaternary ammonium group and the constitution unit (B3) based on a (meth)acrylamide monomer.

[10] The method of [8] or [9] wherein the uncomfortable taste is an uncomfortable taste relating to one or two or more senses of taste selected from the group consisting of bitterness, sweetness, saltiness, umami and sourness.

[11] The method of [10] which is a corrigent for reducing a uncomfortable taste wherein the uncomfortable taste is an uncomfortable taste relating to one or two or more senses of taste selected from the group consisting of sweetness, saltiness, umami and sourness.

[12] The method of [11] wherein the uncomfortable taste is an uncomfortable taste relating to bitterness, sweetness, saltiness, umami and sourness.

[13] The method of any of [8] to [12] wherein the copolymer is added to a composition having an uncomfortable taste.

[14] The method of [13] wherein the composition is a composition for mouth cavity.

[15] The method of [13] or [14] wherein the copolymer is added in a proportion of 0.001-5 mass % relative to the whole composition.

[16] The method of any of [13] to [15] wherein the composition having the uncomfortable taste comprises one or two or more components selected from the group consisting of
1) at least one bitterness component selected from the group consisting of methyl salicylate, epsilon-aminocaproic acid, tranexamic acid, dequalinium chloride, benzalkonium chloride, benzethonium chloride, chlorhexidine hydrochloride, chlorhexidine gluconate, povidoneiodine, polyoxyethylenelauryl ether (8-10 E.O.), sodium lauroylsarcosinate, polyoxyethylene hydrogenated castor oil, sorbitan fatty acid ethylene adduct and tee extract;
2) at least one sweetness component selected from the group consisting of glycyrrhizin acid and a salt thereof;
3) at least one saltiness component selected from the group consisting of potassium nitrate, sodium ascorbate, disodium dihydrogen pyrophosphate, sodium pyrophosphate, and sodium chloride; and
4) at least one sourness component selected from the group consisting of aluminum lactate, ascorbic acid, pyridoxine hydrochloride, malic acid, citric acid, tartaric acid, vitamin C, disodium edetate, trisodium edetate, tetrasodium edetate, sodium citrate, gluconic acid, phosphoric acid, succinic acid and edetic acid.

[17] Use of a copolymer for reducing an uncomfortable taste, the copolymer having a weight average molecular weight of 10,000-5,000,000 and comprising
10-90 mol % of a constitution unit (A1) based on 2-(meth)acryloyloxyethylphosphoryl choline, and
90-10 mol % of at least one kind of constitution unit selected from the group consisting of a constitution unit (B1) based on a (meth)acrylic monomer containing an alkyl group, a constitution unit (B2) based on a (meth)acrylic monomer containing a quaternary ammonium group and a constitution unit (B3) based on a (meth)acrylamide monomer.

[18] The use of [17] wherein the copolymer has a weight average molecular weight of 10,000-5,000,000 and comprises 10-90 mol % of the constitution unit (A1) based on 2-(meth)acryloyloxyethylphosphoryl choline, and
90-10 mol % of at least one kind of constitution unit selected from the group consisting of the constitution unit (B2) based on (meth)acrylic monomer containing a quaternary ammonium group and the constitution unit (B3) based on (meth)acrylamide monomer.

[19] The use of [17] or [18] wherein the uncomfortable taste is an uncomfortable taste relating to one or two or more senses of taste selected from the group consisting of bitterness, sweetness, saltiness, umami and sourness.

[20] The use of [19] which is a corrigent for reducing a uncomfortable taste wherein the uncomfortable taste is an uncomfortable taste relating to one or two or more senses of taste selected from the group consisting of sweetness, saltiness, umami and sourness.

[21] The use of [20] wherein the uncomfortable taste is an uncomfortable taste relating to bitterness, sweetness, saltiness, umami and sourness.

[22] The use of any of [17] to [21] which is for reducing an uncomfortable taste of a composition for mouth cavity.

[23] The use of any of [17] to [22] which is for reducing an uncomfortable taste caused by one or two or more components selected from the group consisting of
1) at least one bitterness component selected from the group consisting of methyl salicylate, epsilon-aminocaproic acid, tranexamic acid, dequalinium chloride, benzalkonium chloride, benzethonium chloride, chlorhexidine hydrochloride, chlorhexidine gluconate, povidoneiodine, polyoxyethylenelauryl ether (8-10 E.O.), sodium lauroylsarcosinate, polyoxyethylene hydrogenated castor oil, sorbitan fatty acid ethylene adduct and tee extract;
2) at least one sweetness component selected from the group consisting of glycyrrhizin acid and a salt thereof;
3) at least one saltiness component selected from the group consisting of potassium nitrate, sodium ascorbate, disodium dihydrogen pyrophosphate, sodium pyrophosphate, and sodium chloride; and
4) at least one sourness component selected from the group consisting of aluminum lactate, ascorbic acid, pyridoxine hydrochloride, malic acid, citric acid, tartaric acid, vitamin C, disodium edetate, trisodium edetate, tetrasodium edetate, sodium citrate, gluconic acid, phosphoric acid, succinic acid and edetic acid.

Effect of the Invention

The present invention makes it possible to provide a corrigent that has no taste at all and reduces an uncomfortable taste while maintaining the balance of tastes of the product and to provide a composition for mouth cavity which contains the corrigent and permits formulation design with highly broad utility. In addition, a composition for mouth cavity with suppressed uncomfortable tastes of the active ingredients can be provided. Furthermore, by using this in combination with a flavor and other artificial sweeteners in preparations for oral care such as mouthwash solution, dentifrice and the like, attractive products for consumers can be provided such as one in which the amounts of surfactant and artificial sweetener to be used are reduced by decreasing the amount of flavor to be added and the like.

DESCRIPTION OF EMBODIMENTS

The present invention is explained in more detail in the following.
<(1) The Corrigent of the Present Invention>
The corrigent of the present invention consists of a copolymer containing
a constitution unit (A) based on 2-(meth)acryloyloxyethyl-phosphoryl choline, and a constitution unit (B1) based on a (meth)acrylic monomer containing an alkyl group, a constitution unit (B2) based on a (meth)acrylic monomer containing a quaternary ammonium group or a constitution unit (B3) based on a (meth)acrylamide monomer.
<The Constitution Unit (A) Based on 2-(Meth)Acryloyloxy-ethylphosphoryl Choline>
The constitution unit (A) based on 2-(meth)acryloyloxy-ethylphosphoryl choline is more specifically a constitution unit induced by polymerization of a monomer represented by the following chemical formula [I].

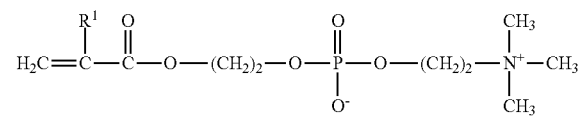
[I]

In the formula [I], $R^1$ is a hydrogen atom or a methyl group.
$R^1$ is preferably a methyl group.
The copolymer to be used in the present invention has the constitution unit (A) in the molecular chain, which enables expression of an effect to inhibit attachment of an uncomfortable taste component to a moiety which receives it. The content of the constitution unit (A) in the copolymer to be used in the present invention is 10-90 mol %, preferably 20-90 mol %, more preferably 35-90 mol %. When the content is too low, the effect to suppress attachment of the uncomfortable tastes will become low and when it is too high, the constitution unit (A) will flow out into water due to its high hydrophilicity, thus resulting in a low effect.
<The Constitution Unit (B1) Based on (Meth)Acrylic Monomer Containing Alkyl Group>
The constitution unit (B1) based on a (meth)acrylic monomer containing an alkyl group is more specifically a constitution unit induced by polymerization of a monomer represented by the following chemical formula [II].

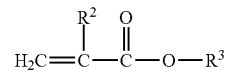
[II]

In the formula [II],
$R^2$ is a hydrogen atom or a methyl group, and
$R^3$ is a hydrogen atom or an alkyl group having a carbon number of 4-18.
$R^2$ is preferably a methyl group.
$R^3$ is preferably a linear or branched alkyl group having a carbon number of 4-18.
Examples of the linear alkyl group having a carbon number 4-18 include n-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group and n-octadecyl group. Examples of the branched alkyl group having a carbon number 4-18 include t-butyl group, isobutyl group, isopentyl group, t-pentyl group, neopentyl group, isohexyl group, isoheptyl group, isooctyl group, isononyl group, isodecyl group, isoundecyl group, isododecyl group, isotridecyl group, isotetradecyl group, isopentadecyl group, isohexadecyl group, isoheptadecyl group, isooctadecyl group and the like.
$R^3$ is more preferably an n-butyl group, an n-dodecyl group, an n-octadecyl group or the like.
Preferable examples of the (meth)acrylic monomer containing an alkyl group include butyl(meth)acrylate, lauryl (meth)acrylate, stearyl(meth)acrylate, 2-ethylhexyl(meth) acrylate and the like.
<The Constitution Unit (B2) Based on (Meth)Acrylic Monomer Containing Quaternary Ammonium Group>
The aforementioned constitution unit (B2) based on a (meth)acrylic monomer containing a quaternary ammonium group is more specifically a constitution unit induced by polymerization of a monomer represented by the following chemical formula [III].

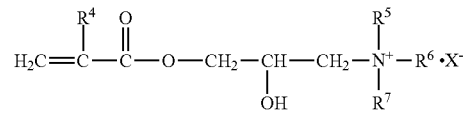
[III]

In the formula [III], $R^4$ is a hydrogen atom or a methyl group, preferably a methyl group. $R^5$, $R^6$ and $R^7$ are each independently a hydrogen atom or an alkyl group having a carbon number of 1-8, and the alkyl group may be any of linear, branched and cyclic. $R^5$, $R^6$ and $R^7$ are preferably alkyl groups having a carbon number of 1-3, more preferably methyl groups. Examples of $X^-$ include halogen ions such as chloride ion and the like and acid residues such as sulfate ion, methylsulfate ion and the like. Of these, halogen ion is preferable.

Preferable examples of the (meth)acrylic monomer containing a quaternary ammonium group include 2-hydroxy-3-methacryloyloxypropyltrimethylammonium chloride and the like.

<The Constitution Unit (B3) Based on (Meth)Acrylamide Monomer>

The aforementioned constitution unit (B3) based on a (meth)acrylamide monomer group is more specifically a constitution unit induced by polymerization of monomers represented by the following chemical formula [IV].

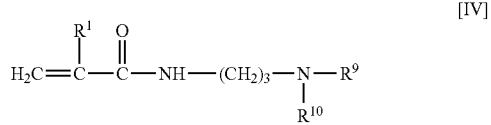

[IV]

In the formula [IV], $R^8$ is a hydrogen atom or a methyl group, $R^9$ and $R^{10}$ are the same or different and each is an alkyl group having a carbon number of 1-6.

$R^8$ is preferably a hydrogen atom.

$R^9$ and $R^{10}$ are preferably the same.

The alkyl group having a carbon number of 1-6 means a linear or branched alkyl group having a carbon number of 1-6.

Specific examples thereof include methyl group, ethyl group, propyl group, isopropyl group, n-butyl group, isobutyl group, sec-butyl group, tert-butyl group, n-pentyl group, isopentyl group, n-hexyl group and the like, with preference given to methyl group.

In a preferable embodiment, in a monomer represented by the formula [IV], $R^8$ is a hydrogen atom and $R^9$ and $R^{10}$ are methyl groups.

Preferable examples of the (meth)acrylamide monomer include N,N-dimethylaminopropylacrylamide and the like.

The copolymer to be used in the present invention has, in the molecular chain, at least one constitution unit selected from the group consisting of (B1), (B2) and (B3) in the molecular chain. The copolymer to be used in the present invention may have, in the molecular chain, any one constitution unit alone selected from the group consisting of (B1), (B2) and (B3), or two constitution units selected from the group consisting of (B1), (B2) and (B3) (e.g., (B1) and (B2), (B1) and (B3), (B2) and (B3)), or optionally has all m constitution units (B1), (B2), and (B3).

The copolymer to be used in the present invention has constitution units (B1)-(B3) in the molecular chain, and therefore, shows property of high retention in the moiety which receives tastes. Furthermore, the copolymer to be used in the present invention having not only (B1)-(B3) but also constituent unit (A) in the same polymer chain provides a corrigent showing suppression of attachment of an uncomfortable taste component to the moiety which receives the taste and appropriate retention property. The contents of the constitution units (B1)-(B3) (when one of the constitution units (B1)-(B3) is contained, the content of said constitution unit, and when 2 or 3 constitution units of (B1)-(B3) are contained, the total contents of these constitution units) in the copolymer to be used in the present invention is 10-90 mol %, preferably 10-80 mol %, more preferably 10-65 mol %. When the content is too low, the effect will be low because the copolymer is highly hydrophilic and flows during use in water and when it is too high, the retention property will be strong and the feeling of use will be deteriorated.

Preferable examples of the combination of constituent unit (A) and constitution units (B1)-(B3) contained in the molecular chain of the copolymer to be used in the present invention are as indicated below. For convenience, the combinations are recited using the names of monomers 2-(meth)acryloyloxyethylphosphoryl choline and butylmethacrylate; 2-(meth)acryloyloxyethylphosphoryl choline and stearylmethacrylate; 2-(meth)acryloyloxyethylphosphoryl choline and 2-hydroxy-3-methacryloyloxypropyltrimethylammonium chloride; and 2-methacryloyloxyethylphosphoryl choline, N,N-dimethylaminopropylacrylamide, and stearylmethacrylate.

The copolymer to be used in the present invention may contain a constituent unit other than the constituent unit (A) and constituent units (B1)-(B3). Preferably, it consists of constituent unit (A), and 1, 2 or 3 constitution units selected from the group consisting of the constitution units (B1), (B2), and (B3).

As the copolymer to be used in the present invention, polymer 1 obtained by polymerization according to the method of JP-A-11-035605, polymer 2 obtained by polymerization according to the method of JP-A-2004-196868, polymer 3 obtained by polymerization according to the method of JP-A-2004-196868, polymer 4 obtained by polymerization according to the method of JP-A-2004-189678, polymer 5 obtained by polymerization according to the method of JP-A-2013-018749 and the like can be used.

The weight average molecular weight of the copolymer to be used in the present invention is 10,000-5,000,000, preferably 50,000-1,000,000. When the weight average molecular weight is too low, an effect comparable to the amount cannot be obtained, and when it is too high, the sense of use will be degraded since the coated feeling becomes too strong when in use and the like while the taste masking effect can be obtained.

The aforementioned copolymer can reduce an uncomfortable taste relating to any of the five basic tastes (bitterness, sweetness, saltiness, umami, sourness), and therefore, can be used as a corrigent to reduce an uncomfortable taste relating to one or two or more (e.g., 2, 3, 4 or 5) senses of tastes selected from the group consisting of bitterness, sweetness, saltiness, umami and sourness. The aforementioned copolymer can be used as a corrigent to reduce an uncomfortable taste relating to one or two or more (e.g., 2, 3, 4 or 5) senses of tastes selected from the basic tastes other than bitterness (sweetness, saltiness, umami and sourness). In addition, the aforementioned copolymer can be used as a corrigent to reduce an uncomfortable taste relating to bitterness caused by a compound other than phenoxyethanol.

The corrigent of the present invention reduces the uncomfortable taste by physically masking the moiety which receives an uncomfortable taste component with the aforementioned copolymer, and inhibiting an uncomfortable taste component from attaching to the receiving moiety. Therefore, it can reduce uncomfortable tastes irrespective of the kind of the uncomfortable taste components.

When the aforementioned copolymer is used as a corrigent, an uncomfortable taste reducing effect can be obtained by blending the copolymer generally at not less than 0.001 mass % relative to the whole composition. When it exceeds 5 mass %, an effect comparable to the amount cannot be achieved. Thus, it is preferably blended at not more than 5 mass %. The copolymer is most preferably used at 0.001 mass % to 2 mass % at which the sense of use such as properties of viscosity and the like of the preparation will not be influenced.

<(2) the Composition for Mouth Cavity of the Present Invention>

The composition for mouth cavity of the present invention contains the aforementioned copolymer as a corrigent. The content of the aforementioned copolymer in the composition for mouth cavity of the present invention is generally 0.001-5 mass %, preferably 0.001-2 mass %.

As mentioned above, the aforementioned copolymer itself has an effect to reduce an uncomfortable taste. Thus, the composition for mouth cavity of the present invention containing the aforementioned copolymer can eliminate an uncomfortable taste in the oral cavity. When the mouth cavity composition of the present invention contains a component causing an uncomfortable taste relating to any of the five basic tastes (bitterness, sweetness, saltiness, umami, sourness), the aforementioned copolymer can mask and reduce the uncomfortable taste caused by the component.

The composition for mouth cavity of the present invention can be applied to products for mouth cavity such as mouthwash solution, oral rinse, dentifrice, oral algefacient and the like and the form thereof is not particularly limited as long as it is a usable form such as liquid, viscose liquid, gel and the like. Even when the corrigent of the present invention is contained in a composition for mouth cavity in the form of an oral preparation not requiring water such as chewable tablet, tablet, capsule and the like, the effect thereof can be expressed as long as water is substantially present when in use. For example, an oral preparation such as chewable tablet, tablet, capsule and the like is coated with the aforementioned copolymer.

The composition for mouth cavity of the present invention preferably contains water as a solvent. The content of water in the composition is generally 30.0-99.9 mass %.

Water as a solvent to be contained in the composition for mouth cavity of the present invention is preferably purified water, pure water, ion exchanged water and the like in view of safety. In addition, ethanol as a lower alcohol, glycerol or sorbitol as a polyhydric alcohol and the like can also be used in combination as a solvent.

Furthermore, the composition for mouth cavity of the present invention contains the aforementioned copolymer as a corrigent, water as a solvent and can contain, where necessary, buffering agent, wetting agent, medicament, surfactant, antiseptic microbicide, sweetening agent, viscosity agent, solvent, dye, organic acid, inorganic salts, antioxidant, stabilizer, preservative, metal ion chelator, flavor, corrigent, water-soluble polysaccharides and the like, which are generally usable for compositions for mouth cavity.

While the buffering agent is not particularly limited, citric acid, phosphoric acid, malic acid, gluconic acid and salts of these can be mentioned. These buffering agents are desirably used at 0.01 mass %-3 mass %.

While the wetting agent is not particularly limited, polyhydric alcohols such as propylene glycol, butyleneglycol, pentyleneglycol, dipropyleneglycol, polyethylene glycol, xylitol, mannitol, erythritol and the like can be mentioned. These polyhydric alcohols are desirably used at 1 mass %-50 mass %.

While the medicament is not particularly limited, anti-inflammatory agents such as sodium azulenesulfonate, allantoin, aluminum chlorohydroxy allantoinate, allantoinhydroxyaluminum, epidihydrocholesterin, dihydrocholesterol, glycyrrhizin acid and a salt thereof, β-glycyrrhetinic acid, lysozyme chloride, methyl salicylate and the like;

hemostasis agents such as epsilon-aminocaproic acid, tranexamic acid and the like;

hypersensitivity mitigation agents such as potassium nitrate, aluminum lactate and the like;

antibacterial agents such as isopropylmethylphenol, dequalinium chloride, benzalkonium chloride, benzethonium chloride, alkyldiaminoethylglycine hydrochloride, chlorhexidine hydrochloride, chlorhexidine gluconate, triclosan, sodium polyphosphate, povidoneiodine, hinokitiol and the like;

expectorants such as 1,8-cineole and the like;

vitamins such as ascorbic acid and a salt thereof, pyridoxine hydrochloride, dl-α-tocopherol acetate, dl-α-tocopherol nicotinate and the like;

adsorbents such as zeolite and the like;

anti-calculsus agents such as disodium dihydrogen pyrophosphate, sodium pyrophosphate, zinc chloride and the like;

agents for preventing dental caries such as sodium fluoride, monofluorosodium phosphate and the like;

agents for eliminating halitosis such as sodium copper chlorophyllin and the like;

detergents such as polyoxyethylenelauryl ether (8-10 E.O.), sodium lauroylsarcosinate and the like;

astringents such as sodium chloride, l-menthol and the like;

agents for eliminating dental plaque such as disodium hydrogen phosphate, trisodium phosphate, polyethylene glycol, polyvinylpyrrolidone and the like;

and the like can be mentioned.

The composition for mouth cavity of the present invention contains the aforementioned copolymer as the corrigent. Therefore, even when glycyrrhizin acid and a salt thereof (sweetness), methyl salicylate (bitterness), epsilon-aminocaproic acid (bitterness), tranexamic acid (bitterness), potassium nitrate (saltiness), aluminum lactate (sourness), dequalinium chloride (bitterness), benzalkonium chloride (bitterness), benzethonium chloride (bitterness), chlorhexidine hydrochloride (bitterness), chlorhexidine gluconate (bitterness), povidoneiodine (bitterness), ascorbic acid (sourness), sodium ascorbate (saltiness), pyridoxine hydrochloride (bitterness, sourness), disodium dihydrogen pyrophosphate (saltiness), sodium pyrophosphate (saltiness), polyoxyethylenelauryl ether (8-10 E.O.) (bitterness), sodium lauroylsarcosinate (bitterness), sodium chloride (saltiness) or the like, from among the aforementioned medicaments, known to cause an uncomfortable taste is contained, the uncomfortable taste thereof is reduced. In one embodiment, the composition for mouth cavity of the present invention contains at least one medicament selected from the group consisting of glycyrrhizin acid and a salt thereof, methyl salicylate, epsilon-aminocaproic acid, tranexamic acid, potassium nitrate, aluminum lactate, dequalinium chloride, benzalkonium chloride, benzethonium chloride, chlorhexidine hydrochloride, chlorhexidine gluconate, povidoneiodine, ascorbic acid, sodium ascorbate, pyridoxine hydrochloride, disodium dihydrogen pyrophosphate, sodium pyrophosphate, polyoxyethylenelauryl ether (8-10 E.O.), sodium lauroylsarcosinate, and sodium chloride (saltiness).

While the surfactant is not particularly limited, polyoxyethylene hydrogenated castor oil, polyoxyethylene alkyl ether, sorbitan fatty acid ethylene adduct, polyglycerol fatty acid ester, glycerol fatty acid ethylene adduct, glycerol fatty acid ester, polyglycerin fatty acid ethylene adduct, polyglycerol fatty acid ester, polyoxyethylene alkyl ether phosphoric acid, polyoxyethylene-polyoxypropylene copolymer, sucrose fatty acid ester, alkylsulfate, polyoxyethylene alkyl ether sulfate, acylamino acid salt, fatty acid aminopropylbetaine, fatty acid amidebetaine and the like can be mentioned. The composition for mouth cavity of the present invention particularly preferably uses 0.05 mass %-2 mass % of polyoxyethylene hydrogenated castor oil or sorbitan fatty acid ethylene adduct. The composition for mouth cavity of the present invention contains the aforementioned copolymer as the corrigent. Therefore, even when polyoxyethylene hydrogenated castor oil (bitterness) or sorbitan fatty acid ethylene adduct (bitterness), from among the aforementioned surfactants, known to cause an uncomfortable taste is contained, the uncomfortable taste thereof is reduced. In one embodiment, the composition for mouth cavity of the present invention contains at least one surfactant selected from polyoxyethylene hydrogenated castor oil and sorbitan fatty acid ethylene adduct.

While the antiseptic microbicide is not particularly limited, polyhexanide hydrochloride, hinokitiol, benzoic acid and a salt thereof, parabens, benzalkonium chloride, benzethonium chloride, povidoneiodine, chlorhexidine gluconate, chlorhexidine hydrochloride, isopropylmethylphenol, triclosan, hinokitiol, salicylic acid and a salt thereof, lysozyme chloride, zinc chloride, alkyldiaminoethylglycine chloride and the like can be mentioned. The amount of the antiseptic microbicide is generally 0.01-1 mass %. The composition for mouth cavity of the present invention contains the aforementioned copolymer as the corrigent. Therefore, even when benzalkonium chloride (bitterness), benzethonium chloride (bitterness), povidoneiodine (bitterness), chlorhexidine gluconate (bitterness) or chlorhexidine hydrochloride (bitterness), from among the aforementioned antiseptic microbicides, known to cause an uncomfortable taste is contained, the uncomfortable taste thereof is reduced. In one embodiment, the composition for mouth cavity of the present invention contains at least one antiseptic microbicide selected from benzalkonium chloride, benzethonium chloride, povidoneiodine, chlorhexidine gluconate and chlorhexidine hydrochloride.

While the sweetening agent is not particularly limited, artificial sweeteners such as sucralose, acesulfame potassium, saccharin, aspartame and the like; stevia, stevioside, revaudioside A, sucrose, licorice extract and the like can be mentioned. The composition for mouth cavity of the present invention contains the aforementioned copolymer as the corrigent. Therefore, the content of the sweetening agent can be reduced, or a smooth sense of taste can be achieved even without containing a sweetening agent. In one embodiment, the composition for mouth cavity of the present invention does not contain a sweetening agent (e.g., artificial sweetener).

While the viscosity agent is not particularly limited, polysaccharides such as cellulose-based viscosity agents such as methylcellulose, hydroxyethylcellulose, hydroxypropylcellulose, hydroxypropylmethylcellulose, carboxymethylcellulose and the like, hyaluronic acid and a salt thereof, chondroitin sulfate and a salt thereof, alginic acid and a salt thereof, gellan gum, xanthan gum and the like, and the like can be mentioned.

While the dye is not particularly limited, for example, titanium oxide, food colors, red iron oxidedye, safflower dye, caramel dye, gardenia dye, tar pigment, chlorophyll and the like can be mentioned.

While the organic acid is not particularly limited, for example, malic acid, citric acid, tartaric acid, ascorbic acid and the like can be mentioned. The composition for mouth cavity of the present invention contains the aforementioned copolymer as the corrigent. Therefore, even when malic acid (sourness), citric acid (sourness), tartaric acid (sourness) or ascorbic acid (sourness), from among the aforementioned organic acids, known to cause an uncomfortable taste is contained, the uncomfortable taste thereof is reduced. In one embodiment, the composition for mouth cavity of the present invention contains at least one organic acid selected from malic acid, citric acid, tartaric acid, and ascorbic acid.

While the antioxidant is not particularly limited, vitamin E, vitamin C, tee extract, rosemary extract and the like can be mentioned. The composition for mouth cavity of the present invention contains the aforementioned copolymer as the corrigent. Therefore, even when vitamin C (sourness) or tee extract (bitterness), from among the aforementioned antioxidants, known to produce an uncomfortable taste is contained, the uncomfortable taste thereof is reduced. In one embodiment, the composition for mouth cavity of the present invention contains at least one antioxidant selected from vitamin C and tee extract.

While the stabilizer is not particularly limited, sodium sulfite, sodium pyrrosulfite, sodium bisulfite, butylhydroxytoluene, propyl gallate, butylhydroxyaryl and the like can be mentioned.

While the metal ion chelator is not particularly limited, 1-hydroxyethane-1,1-diphosphoric acid, tetrasodium 1-hydroxyethane-1,1-diphosphate, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, ethylenediaminehydroxyethyl-triacetic acid trisodium salt and the like can be mentioned. The composition for mouth cavity of the present invention contains the aforementioned copolymer as the corrigent. Therefore, even when disodium edetate (sourness), trisodium edentate (sourness), tetrasodium edetate (sourness), sodium citrate (saltiness), gluconic acid (sourness), phosphoric acid (sourness), citric acid (sourness), ascorbic acid (sourness), succinic acid (sourness) or edetic acid (sourness), from among the aforementioned metal ion chelators, known to produce an uncomfortable taste is contained, the uncomfortable taste thereof is reduced. In one embodiment, the composition for mouth cavity of the present invention contains at least one metal ion chelator selected from disodium edetate, trisodium edetate, tetrasodium edetate, sodium citrate, gluconic acid, phosphoric acid, citric acid, ascorbic acid, succinic acid, and edetic acid.

While the flavor is not particularly limited as long as it is generally contained in compositions for mouth cavity to afford a sensation of coolness, for example, oily components such as peppermint oil, spearmint oil, anise oil, eucalyptus oil, thyme oil, sage oil, peppermint oil and the like, menthol, carvone, anethole, cineole, methyl salicylate, cinnamic aldehyde, eugenol, thymol, menton, menthyl acetate, pinene and the like can be mentioned.

While the corrigent is not particularly limited, for example, fennel extract, turmeric extract, phellodendron bark extract, coptis extract, chlorella extract, cinnamic tincture, kelp extract, Japanese pepper extract, amomum seed extract, ginger extract, edible carrot extract, swertia herb, *perilla* herb extract, ziziphus jujube fruit extract, chili pepper, spruce extract, bitterwood extract, borneol extract, fructose, caramel, licorice, glycyrrhizin acid, trisodium glycyrrhizinate, diammonium glycyrrhizinate, dipotassium glycyrrhizinate, disodium glycyrrhizinate, monoammonium glycyrrhizinate, glutamic acid and a salt thereof, honey, syrup, apple juice, royal jelly, citric acid and a salt thereof and the like can be mentioned. The composition for mouth cavity of the present invention contains the aforementioned copolymer as the corrigent. Therefore, the content of the corrigent other than the copolymer can be reduced, and an uncomfortable taste due to other components can be reduced even without containing a corrigent other than the copolymer. In one embodiment, the composition for mouth cavity of the present invention does not contain a corrigent other than the copolymer.

While the water-soluble polysaccharides are not particularly limited, water-soluble cellulose derivatives such as hydroxypropylmethylcellulose, hydroxyethylcellulose, hydroxypropylcellulose, carboxymethylcellulose and the like, and the like can be mentioned. Water-soluble polysaccharides contained therein function as a binder and strong attachment of the aforementioned copolymer to mouth cavity mucosa and tooth is achieved. The present invention does not require attachment to the mouth cavity mucosa or tooth to exhibit an effect of the aforementioned copolymer to reduce an uncomfortable taste. Therefore, addition of the above-mentioned water-soluble polysaccharides to the composition for mouth cavity of the present invention is not essential.

The composition for mouth cavity of the present invention contains the aforementioned copolymer as the corrigent. Therefore, even when a component having bitterness, sweetness, saltiness, umami or sourness, from among the aforementioned blendable components, known to produce an uncomfortable taste is contained, for example, 1) at least one bitterness component selected from the group consisting of methyl salicylate, epsilon-aminocaproic acid, tranexamic acid, dequalinium chloride, benzalkonium chloride, benzethonium chloride, chlorhexidine hydrochloride, chlorhexidine gluconate, povidoneiodine, polyoxyethylenelauryl ether (8-10 E.O.), sodium lauroylsarcosinate, polyoxyethylene hydrogenated castor oil, sorbitan fatty acid ethylene adduct and tee extract;
2) at least one sweetness component selected from the group consisting of glycyrrhizin acid and a salt thereof;
3) at least one saltiness component selected from the group consisting of potassium nitrate, sodium ascorbate, disodium dihydrogen pyrophosphate, sodium pyrophosphate, and sodium chloride; and
4) at least one sourness component selected from the group consisting of aluminum lactate, ascorbic acid, pyridoxine hydrochloride, malic acid, citric acid, tartaric acid, vitamin C, disodium edetate, trisodium edetate, tetrasodium edetate, sodium citrate, gluconic acid, phosphoric acid, succinic acid and edetic acid,
the uncomfortable taste thereof is reduced.

In one embodiment, the composition for mouth cavity of the present invention contains an agent causing one or two or more uncomfortable tastes selected from the group consisting of, 1) at least one surfactant selected from polyoxyethylene hydrogenated castor oil and sorbitan fatty acid ethylene adduct;
2) at least one antiseptic microbicide selected from benzalkonium chloride, benzethonium chloride, povidoneiodine, chlorhexidine gluconate and chlorhexidine hydrochloride;
3) at least one organic acid selected from malic acid, citric acid, tartaric acid and ascorbic acid;
4) at least one antioxidant selected from vitamin C and tee extract; and
5) at least one metal ion chelator selected from disodium edetate, trisodium edetate, tetrasodium edetate, sodium citrate, gluconic acid, phosphoric acid, citric acid, ascorbic acid, succinic acid and edetic acid.

The aforementioned copolymer can reduce any uncomfortable tastes relating to the five basic tastes (bitterness, sweetness, saltiness, umami, sourness). Therefore, even when the mouth cavity composition of the present invention contains a combination of two or more kinds of components causing an uncomfortable taste relating to a different sense of taste, from among components causing uncomfortable tastes relating to any of the senses of taste relating to the five basic tastes (bitterness, sweetness, saltiness, umami, sourness), it can mask and reduce the uncomfortable tastes caused by said two or more kinds of components. Examples of the combination of two kinds of components include the following.

a component causing an uncomfortable taste relating to bitterness, and a component causing an uncomfortable taste relating to sweetness a component causing an uncomfortable taste relating to bitterness, and a component causing an uncomfortable taste relating to saltiness a component causing an uncomfortable taste relating to bitterness, and a component causing an uncomfortable taste relating to umami a component causing an uncomfortable taste relating to bitterness, and a component causing an uncomfortable taste relating to sourness a component causing an uncomfortable taste relating to sweetness, and a component causing an uncomfortable taste relating to saltiness a component causing an uncomfortable taste relating to sweetness, and a component causing an uncomfortable taste relating to umami a component causing an uncomfortable taste relating to sweetness, and a component causing an uncomfortable taste relating to sourness a component causing an uncomfortable taste relating to saltiness, and a component causing an uncomfortable taste relating to umami a component causing an uncomfortable taste relating to saltiness, and a component causing an uncomfortable taste relating to sourness a component causing an uncomfortable taste relating to umami, and a component causing an uncomfortable taste relating to sourness Specific examples of each component include, but are not limited to, those recited as compounds causing uncomfortable tastes, from among the components mentioned above as components usable for the composition for mouth cavity of the present invention.

Specific examples of the combination of components causing two or more kinds of uncomfortable tastes include, but are not limited to, the following.

polyoxyethylene hydrogenated castor oil, citric acid and sodium citrate polyoxyethylene hydrogenated castor oil and potassium nitrate polyoxyethylene hydrogenated castor oil and dipotassium glycyrrhizinate polyoxyethylene hydrogenated castor oil, citric acid, sodium citrate and dipotassium glycyrrhizinate citric acid and sodium citrate polyoxyethylene hydrogenated castor oil and citric acid polyoxyethylene hydrogenated castor oil and sodium citrate citric acid and dipotassium glycyrrhizinate sodium citrate and dipotassium glycyrrhizinate polyoxyethylene hydrogenated castor oil, citric acid and dipotassium glycyrrhizinate polyoxyethylene hydrogenated castor oil, sodium citrate and dipotassium glycyrrhizinate citric acid, sodium citrate and dipotassium glycyrrhizinate The composition for mouth cavity of the present invention desirably contains 0.005 mass %-1.0 mass % of an oily component such as flavor, ester oil, vegetable oil and the like.

EXAMPLES

Examples 1-1-1-25, Comparative Examples 1-1-1-10

The components of the five basic tastes shown in Tables 1-3 were added to the corrigent components, and the taste masking effect was evaluated.

First, in Examples 1-1-1-25, the corrigent was dissolved in purified water, components (a) of the five basic tastes were successively added, and dissolved by stirring for 5 min.

In Comparative Examples 1-1-1-10, polyvinylpyrrolidone (K=30 or K=90) was dissolved in purified water, component (a) was added, and dissolved by stirring for 5 min.

Examples 2-1-2-8, 2-13-2-20, Comparative Examples 2-4

The components of the five basic tastes shown in Tables 4-6, which are different in the kind from that of Tables 1-3, were added to the corrigent components, and the taste masking effect was evaluated.

In Examples 2-1-2-8, 2-13-2-20, the corrigent and (a) were added to purified water, and dissolved by mixing for 5 min. In Examples 2-9-2-11, a copolymer of 2-methacryloyloxyethylphosphoryl choline and stearylmethacrylate was fed into purified water at 80° C. by small portions, a dispersion was prepared by sonication, cooled to room temperature, and (a) was added and dissolved by stirring for 5 min.

On the other hand, in Comparative Examples 2-1-2-4, polyvinylpyrrolidone (K=30) was dissolved in purified water, (a) was added, and dissolved by stirring for 5 min.

<Evaluation Method (1)>

An aqueous solution (1 mL) of tannic acid (1.00 g) in 99.00 g of purified water not containing a corrigent was placed in the oral cavity, gargled for 10 seconds and spit out. The strength of the taste was taken as 3 points. Then, 1 mL of Example 1-1 was placed in the oral cavity, gargled for 10 seconds and spit out. The strength of the taste was scored as follows. When the point was not more than 2.5 according to according to the following judgment criteria, the presence of a taste masking effect was acknowledged.

<<How to Score>>

1 point: taste was decreased, 2 points: taste was slightly decreased, 3 points: same, 4 points: taste was slightly enhanced, 5 points: taste was enhanced 《Criteria》

≤2.5 points: having taste masking effect 2.5 points<: no taste masking effect

In Examples 1-2-1-5 and Comparative Examples 1-1-1-15, the kind of the five basic tastes was respectively changed, and the strength of the taste was similarly evaluated based on the taste strength when an aqueous solution of the same concentration of the five basic tastes free of the corrigent was used.

<Evaluation Method (2)>

An aqueous solution (1 mL) of chlorhexidine hydrochloride (0.05 g) having an uncomfortable taste (bitterness) in 99.95 g of purified water was placed in the oral cavity, gargled for 10 seconds and spit out. The strength of the taste was taken as 3 points. Then, 1 mL of Example 2-1 was placed in the oral cavity, gargled for 10 seconds and spit out. The strength of the taste was scored as follows. When the point was not more than 2.5 according to according to the following judgment criteria, the presence of a taste masking effect was acknowledged.

<<How to Score>>

1 point: taste was decreased, 2 points: taste was slightly decreased, 3 points: same, 4 points: taste was slightly enhanced, 5 points: taste was enhanced 《Criteria》

≤2.5 points: having taste masking effect 2.5 points<: no taste masking effect

In Examples 2-2-2-20 and Comparative Examples 2-1-2-4, the kind of the uncomfortable taste was respectively changed, and the strength of the taste was similarly evaluated based on the taste strength when an aqueous solution of the same concentration of the five basic tastes free of a corrigent was used.

TABLE 1

| | | Ex. 1-1 | Ex. 1-2 | Ex. 1-3 | Ex. 1-4 | Ex. 1-5 | Ex. 1-6 | Ex. 1-7 | Ex. 1-8 |
|---|---|---|---|---|---|---|---|---|---|
| Component formulation of the composition for mouth cavity (mass %) | corrigent of the present invention polymer 1 | 0.05 | 0.05 | 0.05 | 0.05 | 0.05 | | | |
| | polymer 2 | | | | | | 0.05 | 0.05 | 0.05 |
| | polymer 3 | | | | | | | | |
| | polymer 4 | | | | | | | | |
| | polymer 5 | | | | | | | | |
| | five basic tastes component | | | | | | | | |
| | tannic acid | 1.00 | | | | | 1.00 | | |
| | citric acid | | 1.00 | | | | | 1.00 | |
| | sodium chloride | | | 0.90 | | | | | 0.90 |

TABLE 1-continued

| | | | | | | | | | |
|---|---|---|---|---|---|---|---|---|---|
| | sucrose | | | | 1.00 | | | | |
| | L-glutamic acid Na | | | | | 0.10 | | | |
| | purified water | 98.95 | 98.95 | 99.05 | 98.95 | 99.85 | 98.95 | 98.95 | 99.05 |
| | total | 100.00 | 100.00 | 100.00 | 100.00 | 100.00 | 100.00 | 100.00 | 100.00 |
| Evaluation | taste masking effect | 1.3 | 1.3 | 2.3 | 1.3 | 1.9 | 1.5 | 1.3 | 2.0 |

| | | Ex. 1-9 | Ex. 1-10 | Ex. 1-11 | Ex. 1-12 | Ex. 1-13 | Ex. 1-14 | Ex. 1-15 |
|---|---|---|---|---|---|---|---|---|
| Component formulation of the composition for mouth cavity (mass %) | corrigent of the present invention polymer 1 | | | | | | | |
| | polymer 2 | 0.05 | 0.05 | | | | | |
| | polymer 3 | | | 0.05 | 0.05 | 0.05 | 0.05 | 0.05 |
| | polymer 4 | | | | | | | |
| | polymer 5 | | | | | | | |
| | five basic tastes component | | | | | | | |
| | tannic acid | | | | 1.00 | | | |
| | citric acid | | | | | 1.00 | | |
| | sodium chloride | | | | | | 0.90 | |
| | sucrose | 1.00 | | | | | 1.00 | |
| | L-glutamic acid Na | | 0.10 | | | | | 0.10 |
| | purified water | 98.95 | 99.85 | 98.95 | 98.95 | 99.05 | 98.95 | 99.85 |
| | total | 100.00 | 100.00 | 100.00 | 100.00 | 100.00 | 100.00 | 100.00 |
| Evaluation | taste masking effect | 1.3 | 1.5 | 1.2 | 1.0 | 1.7 | 1.0 | 1.2 |

TABLE 2

| | | Ex. 1-16 | Ex. 1-17 | Ex. 1-18 | Ex. 1-19 | Ex. 1-20 | Ex. 1-21 | Ex. 1-22 | Ex. 1-23 | Ex. 1-24 | Ex. 1-25 |
|---|---|---|---|---|---|---|---|---|---|---|---|
| Component formulation of the composition for mouth cavity (mass %) | corrigent of the present invention polymer 1 | | | | | | | | | | |
| | polymer 2 | | | | | | | | | | |
| | polymer 3 | | | | | | | | | | |
| | polymer 4 | 0.05 | 0.05 | 0.05 | 0.05 | 0.05 | | | | | |
| | polymer 5 | | | | | | 0.05 | 0.05 | 0.05 | 0.05 | 0.05 |
| | five basic tastes component | | | | | | | | | | |
| | tannic acid | 1.00 | | | | | 1.00 | | | | |
| | citric acid | | 1.00 | | | | | 1.00 | | | |
| | sodium chloride | | | 0.90 | | | | | 0.90 | | |
| | sucrose | | | | 1.00 | | | | | 1.00 | |

TABLE 2-continued

|  |  | Ex. 1-16 | Ex. 1-17 | Ex. 1-18 | Ex. 1-19 | Ex. 1-20 | Ex. 1-21 | Ex. 1-22 | Ex. 1-23 | Ex. 1-24 | Ex. 1-25 |
|---|---|---|---|---|---|---|---|---|---|---|---|
|  | L-glutamic acid Na |  |  |  |  | 0.10 |  |  |  |  | 0.10 |
|  | purified water | 98.95 | 98.95 | 99.05 | 98.95 | 99.85 | 98.95 | 98.95 | 99.05 | 98.95 | 99.85 |
|  | total | 100.00 | 100.00 | 100.00 | 100.00 | 100.00 | 100.00 | 100.00 | 100.00 | 100.00 | 100.00 |
| Evaluation | taste masking effect | 1.0 | 1.0 | 1.0 | 1.0 | 1.0 | 1.8 | 1.8 | 2.4 | 1.3 | 1.8 |

TABLE 3

|  |  | Comp. Ex. 1-1 | Comp. Ex. 1-2 | Comp. Ex. 1-3 | Comp. Ex. 1-4 | Comp. Ex. 1-5 | Comp. Ex. 1-6 | Comp. Ex. 1-7 | Comp. Ex. 1-8 |
|---|---|---|---|---|---|---|---|---|---|
| Component formulation of the composition for mouth cavity (mass %) | corrigent of the present invention |  |  |  |  |  |  |  |  |
|  | MPC homopolymer | 0.05 | 0.05 | 0.05 | 0.05 | 0.05 |  |  |  |
|  | polyvinyl-pyrrolidone (K = 30) |  |  |  |  |  | 0.05 | 0.05 | 0.05 |
|  | hypromellose |  |  |  |  |  |  |  |  |
|  | five basic tastes component |  |  |  |  |  |  |  |  |
|  | tannic acid | 1.00 |  |  |  |  | 1.00 |  |  |
|  | citric acid |  | 1.00 |  |  |  |  | 1.00 |  |
|  | sodium chloride |  |  | 0.90 |  |  |  |  | 0.90 |
|  | sucrose |  |  |  | 1.00 |  |  |  |  |
|  | L-glutamic acid Na |  |  |  |  | 0.10 |  |  |  |
|  | purified water | 98.95 | 98.95 | 99.05 | 98.95 | 99.85 | 98.95 | 98.95 | 99.05 |
| Evaluation | total | 100.00 | 100.00 | 100.00 | 100.00 | 100.00 | 100.00 | 100.00 | 100.00 |
|  | taste masking effect | 2.7 | 2.5 | 2.8 | 2.6 | 2.8 | 3.1 | 3.1 | 3.1 |

|  |  | Comp. Ex. 1-9 | Comp. Ex. 1-10 | Comp. Ex. 1-11 | Comp. Ex. 1-12 | Comp. Ex. 1-13 | Comp. Ex. 1-14 | Comp. Ex. 1-15 |
|---|---|---|---|---|---|---|---|---|
| Component formulation of the composition for mouth cavity (mass %) | corrigent of the present invention |  |  |  |  |  |  |  |
|  | MPC homopolymer | 0.05 | 0.05 |  |  |  |  |  |
|  | polyvinyl-pyrrolidone (K = 30) |  |  |  |  |  |  |  |
|  | hypromellose |  |  | 0.05 | 0.05 | 0.05 | 0.05 | 0.05 |
|  | five basic tastes component |  |  |  |  |  |  |  |
|  | tannic acid |  |  | 1.00 |  |  |  |  |
|  | citric acid |  |  |  | 1.00 |  |  |  |
|  | sodium chloride |  |  |  |  | 0.90 |  |  |
|  | sucrose | 1.00 |  |  |  |  | 1.00 |  |
|  | L-glutamic acid Na |  | 0.10 |  |  |  |  | 0.10 |
|  | purified water | 98.95 | 99.85 | 98.95 | 98.95 | 99.05 | 98.95 | 99.85 |
| Evaluation | total | 100.00 | 100.00 | 100.00 | 100.00 | 100.00 | 100.00 | 100.00 |
|  | taste masking effect | 3.3 | 3.3 | 2.7 | 3.0 | 3.0 | 3.3 | 3.3 |

TABLE 4

| | | Ex. 2-1 | Ex. 2-2 | Ex. 2-3 | Ex. 2-4 | Ex. 2-5 | Ex. 2-6 | Ex. 2-7 | Ex. 2-8 | Ex. 2-9 | Ex. 2-10 |
|---|---|---|---|---|---|---|---|---|---|---|---|
| Component formulation of the composition for mouth cavity (mass %) | corrigent of the present invention polymer 1 | 0.05 | 0.05 | 0.05 | 0.05 | | | | | | |
| | polymer 2 | | | | | 0.05 | 0.05 | 0.05 | 0.05 | | |
| | polymer 3 | | | | | | | | | 0.05 | 0.05 |
| | polymer 4 | | | | | | | | | | |
| | polymer 5 | | | | | | | | | | |
| | five basic tastes component | | | | | | | | | | |
| | chlorhexidine hydrochloride | 0.05 | | | | 0.05 | | | | 0.05 | |
| | benzethonium chloride | | 0.01 | | | | 0.01 | | | | 0.01 |
| | povidoneiodine | | | 6.80 | | | | 6.80 | | | |
| | polyoxyethylene hydrogenated castor oil 60 | | | | 1.00 | | | | 1.00 | | |
| | purified water | 99.90 | 99.94 | 93.15 | 98.95 | 99.90 | 99.94 | 93.15 | 98.95 | 99.90 | 99.94 |
| | total | 100.00 | 100.00 | 100.00 | 100.00 | 100.00 | 100.00 | 100.00 | 100.00 | 100.00 | 100.00 |
| Evaluation | taste masking effect | 1.5 | 1.2 | 1.4 | 1.6 | 1.3 | 1.1 | 1.2 | 1.4 | 2.1 | 2.2 |

TABLE 5

| | | Ex. 2-11 | Ex. 2-12 | Ex. 2-13 | Ex. 2-14 | Ex. 2-15 | Ex. 2-16 | Ex. 2-17 | Ex. 2-18 | Ex. 2-19 | Ex. 2-20 |
|---|---|---|---|---|---|---|---|---|---|---|---|
| Component formulation of the composition for mouth cavity (mass %) | corrigent of the present invention polymer 1 | | | | | | | | | | |
| | polymer 2 | | | | | | | | | | |
| | polymer 3 | 0.05 | 0.05 | | | | | | | | |
| | polymer 4 | | | 0.05 | 0.05 | 0.05 | 0.05 | | | | |
| | polymer 5 | | | | | | | 0.05 | 0.05 | 0.05 | 0.05 |
| | five basic tastes component | | | | | | | | | | |
| | chlorhexidine hydrochloride | | | 0.05 | | | | 0.05 | | | |
| | benzethonium chloride | | | | 0.01 | | | | 0.01 | | |
| | povidoneiodine | 6.80 | | | | 6.80 | | | | 6.80 | |
| | polyoxyethylene hydrogenated castor oil60 | | 1.00 | | | | 1.00 | | | | 1.00 |
| | purified water | 93.15 | 98.95 | 99.90 | 99.94 | 93.15 | 98.95 | 99.90 | 99.94 | 93.15 | 98.95 |
| | total | 100.00 | 100.00 | 100.00 | 100.00 | 100.00 | 100.00 | 100.00 | 100.00 | 100.00 | 100.00 |
| Evaluation | taste masking effect | 2.4 | 2.3 | 1.2 | 1.1 | 1.2 | 1.1 | 1.5 | 1.3 | 1.4 | 1.6 |

TABLE 6

| | | Comp. Ex. 2-1 | Comp. Ex. 2-2 | Comp. Ex. 2-3 | Comp. Ex. 2-4 |
|---|---|---|---|---|---|
| Component formulatin of the composition for mouth cavity (mass %) | corrigent other than the present invention polyvinyl-pyrrolidone (K = 90) | 0.10 | 0.10 | 0.10 | 0.10 |
| | five basic tastes component | | | | |
| | chlorhexidine hydrochloride | 0.05 | | | |
| | benzethonium chloride | | 0.01 | | |
| | povidoneiodine | | | 6.80 | |
| | polyoxyethylene hydrogenated castor oil60 | | | | 1.00 |
| | purified water | 99.85 | 99.89 | 93.10 | 98.90 |
| | total | 100.00 | 100.00 | 100.00 | 100.00 |
| Evaluation | taste masking effect | 2.9 | 3.0 | 3.0 | 3.0 |

The details of the copolymers indicated with abbreviations in the Tables are as follows.

Polymer 1: 2-methacryloyloxyethylphosphocholine.butylmethacrylate copolymer [copolymerization composition ratio (molar ratio) 80/20, weight average molecular weight: 600,000], obtained by polymerization according to the method described in the Example of JP-A-11-035605.

Polymer 2: 2-methacryloyloxyethylphosphocholine.butylmethacrylate copolymer [copolymerization composition ratio (molar ratio) 30/70, weight average molecular weight: 142,000], obtained by polymerization according to the method described in the Example of JP-A-2004-196868.

Polymer 3: 2-methacryloyloxyethylphosphocholine.stearylmethacrylate copolymer [copolymerization composition (molar ratio) 33/67, weight average molecular weight: 164,000], obtained by polymerization according to the method described in the Example of JP-A-2004-196868.

Polymer 4: 2-methacryloyloxyethylphosphoryl choline.2-hydroxy-3-methacryloyloxypropyltrimethylammonium copolymer [copolymerization composition (molar ratio) 70/30, weight average molecular weight: 450,000], obtained by polymerization according to the method described in the Example of JP-A-2004-189678.

Polymer 5: 2-methacryloyloxyethylphosphoryl choline.N,N-dimethylaminopropylacrylamide.stearylmethacrylate copolymer [copolymerization composition (molar ratio) 90/2/8, weight average molecular weight: 820,000], obtained by polymerization according to the method described in the Example of JP-A-2013-018749.

<Evaluation Results (1)>

In Examples 1-1-1-25, the above-mentioned polymers 1-5 were used, and a taste masking effect on the five basic tastes including bitterness (tannic acid), sourness (citric acid), saltiness (sodium chloride), sweetness (sucrose), umami (L-glutamic acid Na) was confirmed by the above-mentioned evaluation method, whereby the function of the polymers as a corrigent was confirmed. As a result, use of the copolymers was found to show a taste masking effect to reduce respective tastes. In all of the five basic tastes, the evaluation point was not more than 2.4, fulfilling the criteria, and the taste masking effect was acknowledged.

On the other hand, in Comparative Examples 1-1-1-5, homopolymers of 2-methacryloyloxyethylphosphoryl choline were used to perform a similar evaluation. As a result, the homopolymers showed 2.5 points for sourness, fulfilling the criteria, but 2.6-2.8 points for other tastes. This shows that the homopolymers were inconsistent in the effect depending on the kind of the taste.

In Comparative Examples 1-6-1-10, moreover, a similar evaluation was performed using polyvinylpyrrolidone (K=90) and using hypromellose in Comparative Examples 1-11-1-15 to obtain not less than 2.7 points, and a taste masking effect was not obtained.

<Evaluation Results (2)>

In Examples 2-1-2-20, the point was 1.1-2.4, which was not more than 2.5, irrespective of the kind of MPC copolymer, thus fulfilling the criteria of taste masking effect.

On the other hand, in Comparative Examples 2-1-2-4, polyvinylpyrrolidone (K=90) was used to perform a similar evaluation. As a result, the point in Comparative Examples was 2.9-3, and an effect to reduce an uncomfortable taste such as bitterness of chlorhexidine hydrochloride, benzethonium chloride, povidoneiodine, polyoxyethylene hydrogenated castor oil and the like as sterilizing components and surfactants was not obtained.

<Evaluation Results (3)>

Using Examples 3-1-3-10, the function of the above-mentioned polymer 1 as a corrigent was confirmed. The evaluation results of the taste masking effect were 1.0-2.0 points, and not more than 2.5 by using a composition for mouth cavity that was blended mimicking a commercially available product, thus fulfilling the criteria of taste masking effect (Table 7).

While the commercially available product included one containing the aforementioned uncomfortable taste components in combination, a taste masking effect was acknowledged (Table 7).

On the other hand, the compositions for mouth cavity (Examples 3-7) containing a stimulating component not classified as the aforementioned uncomfortable taste component showed a decrease in the taste, which is an effect of the corrigent, because excessive stimulation by algefacient became mild due to the corrigent (Table 7).

TABLE 7

| component | Example 3-1 | Example 3-2 | Example 3-3 | Example 3-4 | Example 3-5 | Example 3-6 | Example 3-7 | Example 3-8 | Example 3-9 | Example 3-10 |
|---|---|---|---|---|---|---|---|---|---|---|
| corrigent of the present invention | | | | | | | | | | |
| polymer 1 | 0.50 | 0.50 | 0.50 | 0.50 | 0.50 | 0.50 | 0.50 | 0.50 | 0.50 | 0.50 |
| uncomfortable taste component | | | | | | | | | | |
| bitterness | | | | | | | | | | |
| polyoxyethylene hydrogenated castor oil | 1.00 | | 1.00 | 1.00 | 1.00 | 1.00 | | 1.00 | | |
| benzethonium chloride | | 0.01 | | | | | | | | |
| sourness | | | | | | | | | | |
| citric acid | | | 0.01 | | | 0.01 | | 0.01 | 0.05 | 0.01 |
| disodium edetate | | | | | 0.05 | | | | | |
| saltiness | | | | | | | | | | |
| sodium citrate | | | 0.30 | | | 0.30 | | 0.30 | | 0.30 |
| potassium nitrate | | | | 2.50 | | | | | | |
| sweetness | | | | | | | | | | |
| dipotassium glycyrrhizinate | | | | | | 0.24 | 0.24 | | | |
| other components | | | | | | | | | | |
| isopropylmethylphenol | | | | | | | | | 0.06 | |
| cetylpyridinium chloride | | | 0.05 | | | | | | | |
| triclosan | | | | | 0.02 | | | | | 0.02 |

TABLE 7-continued

| component | Example 3-1 | Example 3-2 | Example 3-3 | Example 3-4 | Example 3-5 | Example 3-6 | Example 3-7 | Example 3-8 | Example 3-9 | Example 3-10 |
|---|---|---|---|---|---|---|---|---|---|---|
| 1,8-cineole | | | | | | | 0.02 | | | |
| thymol | | | | | | | 0.75 | | | |
| 1-menthol | | | | | 0.20 | | 0.75 | | | |
| lauroyl sarcosine Na | | | | | | | | 0.20 | | |
| epsilon-aminocaproic acid | | | | | | | | 0.20 | | |
| methyl salicylate | | | | | | | 0.20 | | | |
| hinokitiol | | | | | 0.05 | | | | | |
| ethanol | 10.00 | | 10.00 | | 10.00 | 10.00 | 25.00 | | | |
| glycerol | 10.00 | 5.00 | 5.00 | 5.00 | | 5.00 | | 8.00 | 6.00 | 5.00 |
| propylene glycol | | 5.00 | | 5.00 | | | | 3.00 | 5.00 | 5.00 |
| PEG8 | | | | | | | | 0.50 | | |
| coconut oil fatty acid acylarginine ethyl·DL-PCA salt | | | | | | 0.10 | | | | |
| glycerol fatty acid ester | | 0.45 | 0.45 | | | | | | | |
| sucrose fatty acid ester | | | 0.45 | | | | | | | |
| soapberry extract | | | | | 0.10 | | | | | |
| erythritol | | | 5.00 | | | | | | | |
| Sodium triphosphate (TPP) | 0.10 | | | | | | | | | |
| polyoxyethylene-polyoxypropyleneglycol | | | | | | | 0.20 | | 0.20 | 0.20 |
| alginic acid PG | | | | | | | | 0.20 | | |
| hydroxyethylcellulose | | | 0.20 | | | | | | | |
| sodium hydrogen phosphate hydrate | 0.30 | 0.30 | | 0.30 | | | | | | |
| disodium hydrogen phosphate | 0.45 | 0.45 | | 0.45 | | | | | | |
| stearyl glycyrrhetinate | | | | | 0.20 | | | | | |
| 2-alkyl-N-carboxymethyl-N-hydroxyethylimidazolinium betaine | | | | | 0.10 | | | | | |
| sodium hexamethaphosphate | | | | | | | | | | 0.10 |
| copper chlorophyllin sodium | 0.0001 | | | | | | | | | |
| xylitol | 5.00 | | | 5.00 | | | | 5.00 | | |
| sorbit solution | | | 5.00 | 5.00 | | | 10.00 | | 5.00 | |
| maltitol | | | 3.00 | | | | | | | |
| erythritol | | | 12.00 | | | | | | | |
| sucralose | | | 3.00 | | | | | | | |
| flavor | 0.10 | 0.10 | 0.10 | 0.10 | 0.10 | 0.10 | 0.10 | 0.10 | 0.10 | 0.10 |
| paraben | 0.10 | 0.10 | | 0.10 | 0.10 | | | 0.10 | | |
| sodium benzoate | | | | | | | | 0.15 | | |
| benzoic acid | | | | | | | 0.10 | | | |
| potassium sorbate | | | | | | | | | 0.10 | |
| saccharin sodium | 0.05 | 0.05 | | 0.05 | | 0.05 | 0.05 | 0.05 | 0.05 | 0.05 |
| dye | 0.10 | | | | | | | 0.10 | 0.10 | |
| Angelica acutiloba extract | | | | | 0.10 | | | | | |
| peony extract | | | | | 0.10 | | | | | |
| water | 72.30 | 88.04 | 53.92 | 75.00 | 87.16 | 82.68 | 62.23 | 80.63 | 82.90 | 88.74 |
| total | 100.00 | 100.00 | 100.00 | 100.00 | 100.00 | 100.00 | 100.00 | 100.00 | 100.00 | 100.00 |
| taste masking effect | 1.0 | 2.0 | 2.0 | 2.0 | 2.0 | 2.0 | 2.0 | 1.0 | 1.0 | 1.0 |

INDUSTRIAL APPLICABILITY

The present invention makes it possible to provide a corrigent that has no taste at all and reduces an uncomfortable taste while maintaining the balance of tastes of the product and a composition for mouth cavity that contains the corrigent and permits formulation design with highly broad utility. In addition, a composition for mouth cavity wherein an uncomfortable taste of the active ingredient is suppressed can be provided. Furthermore, by using this in combination with a flavor and other artificial sweeteners in preparations for oral care such as mouthwash solution, dentifrice and the like, attractive products for consumers can be provided such as one in which the amounts of surfactant and artificial sweetener to be used are reduced by decreasing the amount of flavor to be added and the like.

The contents disclosed in any publication cited in the present specification, including patents and patent applications, are hereby incorporated in their entireties by reference, to the extent that they have been disclosed herein.

This application is based on a patent application No. 2015-131083 filed in Japan (filing date: Jun. 30, 2015), the contents of which are incorporated in full herein.

The invention claimed is:

1. A method of reducing an uncomfortable taste in an oral cavity of a subject in need thereof, which comprises
providing a composition comprising a copolymer having a weight average molecular weight of 10,000-5,000,000 and 10-90 mol % of a constitution unit (A1) based on 2-(meth)acryloyloxyethylphosphoryl choline, and
90-10 mol % of at least one kind of constitution unit selected from the group consisting of a constitution unit (B1) based on a (meth)acrylic monomer containing an alkyl group, a constitution unit (B2) based on a (meth)acrylic monomer containing a quaternary ammonium group and a constitution unit (B3) based on a (meth)acrylamide monomer and
contacting the oral cavity with the composition to reduce the uncomfortable taste in the oral cavity.

2. The method according to claim 1 wherein the copolymer has a weight average molecular weight of 10,000-5,000,000 and comprises
10-90 mol % of the constitution unit (A1) based on 2-(meth)acryloyloxyethylphosphoryl choline, and
90-10 mol % of at least one kind of constitution unit selected from the group consisting of the constitution unit (B2) based on a (meth)acrylic monomer containing a quaternary ammonium group and the constitution unit (B3) based on a (meth)acrylamide monomer.

3. The method according to claim 1 wherein the uncomfortable taste is an uncomfortable taste relating to one or two or more senses of taste selected from the group consisting of bitterness, sweetness, saltiness, umami and sourness.

4. The method according to claim 3 wherein the uncomfortable taste is an uncomfortable taste relating to one or two or more senses of taste selected from the group consisting of sweetness, saltiness, umami and sourness.

5. The method according to claim 3 wherein the uncomfortable taste is an uncomfortable taste relating to bitterness, sweetness, saltiness, umami and sourness.

6. The method according to claim 1 wherein the copolymer is added to a composition having an uncomfortable taste.

7. The method according to claim 6 wherein the composition is a composition for mouth cavity.

8. The method according to claim 6 wherein the copolymer is added in a proportion of 0.001-5 mass % relative to the whole composition.

9. The method according to claim 6 wherein the composition having the uncomfortable taste comprises one or two or more components selected from the group consisting of
1) at least one bitterness component selected from the group consisting of methyl salicylate, epsilon-aminocaproic acid, tranexamic acid, dequalinium chloride, benzalkonium chloride, benzethonium chloride, chlorhexidine hydrochloride, chlorhexidine gluconate, povidoneiodine, polyoxyethylenelauryl ether(8-10 E.O.), sodium lauroylsarcosinate, polyoxyethylene hydrogenated castor oil, sorbitan fatty acid ethylene adduct and tea extract;
2) at least one sweetness component selected from the group consisting of glycyrrhizin acid and a salt thereof;
3) at least one saltiness component selected from the group consisting of potassium nitrate, sodium ascorbate, disodium dihydrogen pyrophosphate, sodium pyrophosphate, and sodium chloride; and
4) at least one sourness component selected from the group consisting of aluminum lactate, ascorbic acid, pyridoxine hydrochloride, malic acid, citric acid, tartaric acid, vitamin C, disodium edetate, trisodium edetate, tetrasodium edetate, sodium citrate, gluconic acid, phosphoric acid, succinic acid and edetic acid.

10. The method according to claim 6 wherein the uncomfortable taste is an uncomfortable taste relating to one or two or more senses of taste selected from the group consisting of bitterness, sweetness, saltiness, umami and sourness.

11. The method according to claim 10 wherein the uncomfortable taste is an uncomfortable taste relating to one or two or more senses of taste selected from the group consisting of sweetness, saltiness, umami and sourness.

12. The method according to claim 10 wherein the uncomfortable taste is an uncomfortable taste relating to bitterness, sweetness, saltiness, umami and sourness.

* * * * *